(12) United States Patent
Lee et al.

(10) Patent No.: US 12,075,564 B2
(45) Date of Patent: Aug. 27, 2024

(54) ELECTRONIC TEXTILES AND METHODS FOR FABRICATION THEREOF

(71) Applicant: Purdue Research Foundation, West Lafayette, IN (US)

(72) Inventors: Chi Hwan Lee, West Lafayette, IN (US); Laurent Couetil, West Lafayette, IN (US); Tae Hoo Chang, Beavercreek, OH (US); Semih Akin, West Lafayette, IN (US); Martin Byung-Guk Jun, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 199 days.

(21) Appl. No.: 17/823,021

(22) Filed: Aug. 29, 2022

(65) Prior Publication Data

US 2023/0136666 A1   May 4, 2023

Related U.S. Application Data

(60) Provisional application No. 63/273,534, filed on Oct. 29, 2021.

(51) Int. Cl.
*H05K 1/03* (2006.01)
*A61B 5/27* (2021.01)
(Continued)

(52) U.S. Cl.
CPC ............... *H05K 1/038* (2013.01); *A61B 5/27* (2021.01); *D06B 11/0059* (2013.01);
(Continued)

(58) Field of Classification Search
CPC .......... H05K 1/038; H05K 1/092; H05K 3/14; H05K 2201/10151; H05K 1/097;
(Continued)

(56) References Cited

U.S. PATENT DOCUMENTS

| 10,722,160 B2 * | 7/2020 | Wang ................... A61B 5/1486 |
| 2004/0189170 A1 * | 9/2004 | Aisenbrey ............. H05K 3/101 313/248 |

(Continued)

OTHER PUBLICATIONS

Akin, S. et al. Dual Regime Spray Deposition Based Laser Direct Writing of Metal Patterns on Polymer Substrates. J. Micro Nano-Manufacturing 8, 024511 (2020).
(Continued)

*Primary Examiner* — Hoa C Nguyen
(74) *Attorney, Agent, or Firm* — Hartman Global IP Law; Gary M. Hartman; Domenica N. S. Hartman

(57) ABSTRACT

Electronic textiles and methods of fabrication electronic textiles. Nanoparticles of a conductive material are sprayed along a conductive path into a fabric material so as to penetrate into the fabric. A layer of a second conductor material is coated over the nanoparticles along the conductive path. A layer of an insulator material is coated over the layer of the second conductor material so as to encapsulate the conductive path and form a trace. An electrode configured to contact a subject wearing the fabric material includes a layer of a third conductor material coated over the layer of the second conductor and electrically coupled with the conductive path. An electrical connector is secured to the fabric material and electrically coupled with the conductive path. The nanoparticles are sprayed onto the fabric material using a dual regime spray process implemented with a dual regime spray system.

19 Claims, 13 Drawing Sheets

(51) Int. Cl.

| | | |
|---|---|---|
| *D06B 11/00* | (2006.01) | |
| *D06M 11/65* | (2006.01) | |
| *D06M 11/83* | (2006.01) | |
| *D06M 15/693* | (2006.01) | |
| *D06M 23/08* | (2006.01) | |
| *H01B 3/28* | (2006.01) | |
| *H05K 1/09* | (2006.01) | |
| *H05K 3/14* | (2006.01) | |
| *D06M 101/06* | (2006.01) | |
| *D06M 101/32* | (2006.01) | |
| *D06M 101/38* | (2006.01) | |

(52) U.S. Cl.
CPC ............ *D06M 11/65* (2013.01); *D06M 11/83* (2013.01); *D06M 15/693* (2013.01); *D06M 23/08* (2013.01); *H01B 3/28* (2013.01); *H05K 1/092* (2013.01); *H05K 3/14* (2013.01); *A61B 2503/40* (2013.01); *A61B 2562/0215* (2017.08); *A61B 2562/0285* (2013.01); *D06M 2101/06* (2013.01); *D06M 2101/32* (2013.01); *D06M 2101/38* (2013.01); *D10B 2201/02* (2013.01); *D10B 2331/04* (2013.01); *D10B 2331/10* (2013.01); *D10B 2401/16* (2013.01); *H05K 2201/10151* (2013.01)

(58) Field of Classification Search
CPC ..... H05K 2201/0257; H05K 2201/026; H05K 2201/0373; H05K 2201/2072; H05K 2203/0307; A61B 2018/00125; A61B 2562/0285

See application file for complete search history.

(56) References Cited

U.S. PATENT DOCUMENTS

| | | | |
|---|---|---|---|
| 2006/0163744 A1* | 7/2006 | Vanheusden | H01L 23/49883 |
| | | | 257/E21.174 |
| 2016/0374411 A1* | 12/2016 | Brooks | A61F 7/007 |
| | | | 165/104.21 |
| 2017/0086513 A1* | 3/2017 | Maxey | A41D 1/04 |
| 2018/0263521 A1* | 9/2018 | Stordopoulos | A61B 5/316 |
| 2019/0167192 A1* | 6/2019 | Frouin | A61B 5/25 |
| 2019/0326656 A1* | 10/2019 | Sotzing | C09D 165/00 |

OTHER PUBLICATIONS

Cao, R. et al. Screen-Printed Washable Electronic Textiles as Self-Powered Touch/Gesture Tribo-Sensors for Intelligent Human-Machine Interaction. ACS Nano 12, 5190-5196 (2018).

Jin, H. et al. Enhancing the Performance of Stretchable Conductors for E-textiles By Controlled Ink Permeation. Adv. Mater. 29, 1605848 (2017).

* cited by examiner

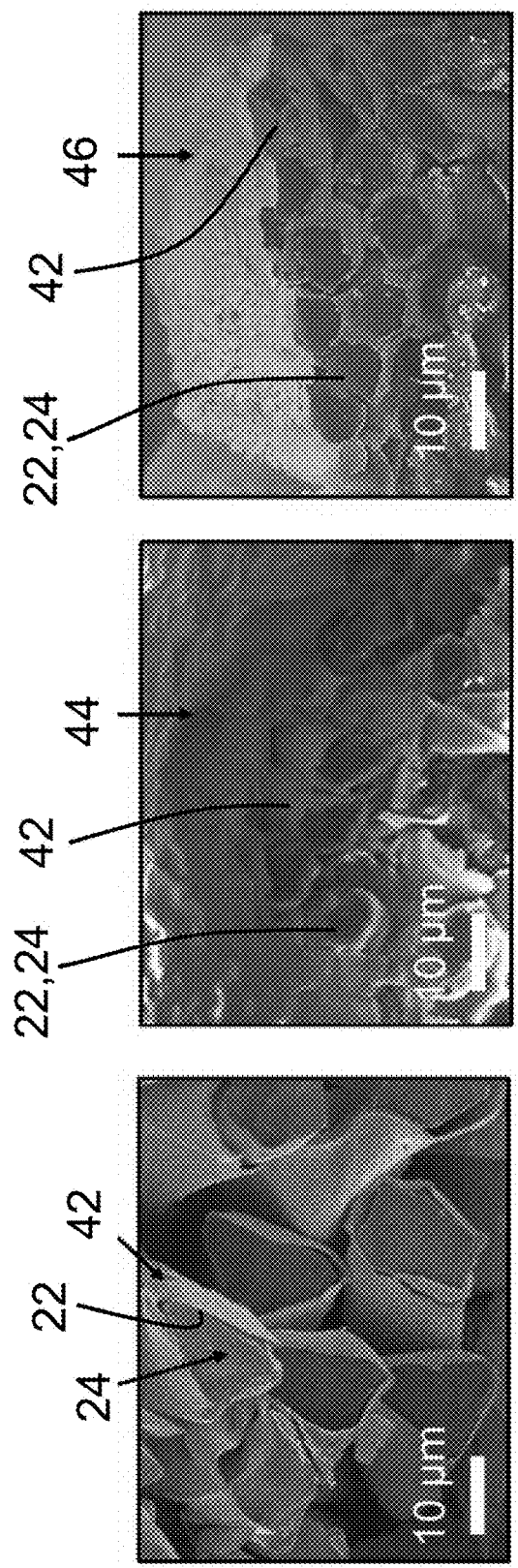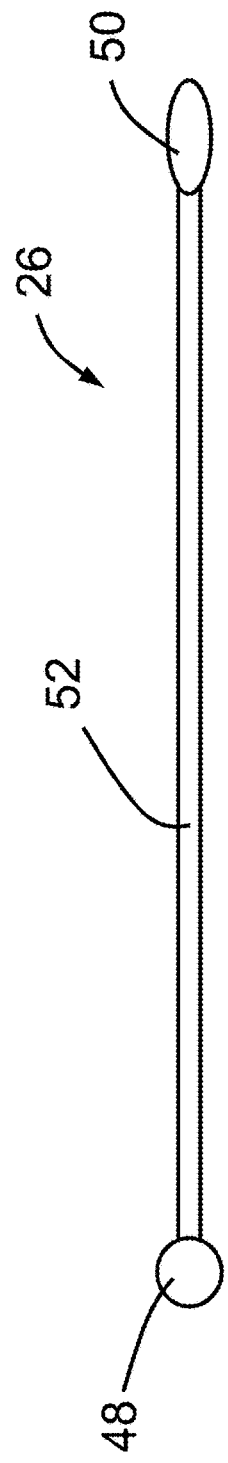

ELECTRONIC TEXTILES AND METHODS FOR FABRICATION THEREOF

CROSS-REFERENCE TO RELATED APPLICATIONS

This application claims the benefit of Provisional U.S. Patent Application No. 63/273,534, filed Oct. 29, 2021, the contents of which are incorporated herein by reference.

STATEMENT REGARDING FEDERALLY SPONSORED RESEARCH OR DEVELOPMENT

This invention was made with government support under EB026099 awarded by the National Institutes of Health. This invention was also made with government support under CMMI 1928784 awarded by the National Science Foundation. The government has certain rights in the invention.

BACKGROUND OF THE INVENTION

The present invention generally relates to electronic textiles and methods of fabrication thereof.

Electronic textiles (also called "e-textiles") are of particular interest in remote healthcare (telehealth) monitoring settings, enabling the ambulatory monitoring of health conditions or disease progression on a routine and/or continuous basis. E-textiles are typically formed through the additive patterning of functional nanomaterials such as conducting nanomaterials, polymers, and ceramics into fabrics in a manner that affords multimodal detection of physiological and electrophysiological responses on the skin. Previous approaches in producing e-textiles involve the use of either wet-spinning, biscrolling, dip-coating, screen-printing, inkjet printing, dip pen nanolithography, physical vacuum depositing, or weaving to overcoat fabrics with functional nanomaterials. Here, precise control of overcoat uniformity and durability is a key to ensure the electrical conductivity and mechanical robustness of the e-textiles during use in ambulatory health monitoring.

Despite great promises, these previous approaches tend to lack large-scale batch production of custom sensor designs, high spatial resolution, reliable electrical connections, and long-term durability (e.g., resistance to aggregation and/or delamination due to use and/or cleaning). These limitations create difficulties for pragmatic deployment of e-textiles in clinical practice.

In view of the above, it would be desirable if systems and/or methods were available for producing e-textiles that were capable of at least partly overcoming or avoiding the shortcomings noted above.

BRIEF DESCRIPTION OF THE INVENTION

The present invention provides electronic textiles and methods for their fabrication.

According to one aspect of the invention, an electronic textile is provided. The electronic textile includes a fabric material configured to be worn by a subject. A conductive path includes nanoparticles comprising a first conductor material penetrated into the fabric material along the conductive path and a layer of a second conductor material coated over the nanoparticles along the conductive path. An electrode is electrically coupled with the conductive path. The electrode includes a layer of a third conductor material coated over the layer of the second conductor at a first portion of the conductive path. The electrode is configured to contact and provide an electrical connection with the subject while the subject is wearing the fabric material. An electrical connector is secured to the fabric material and electrically coupled with the conductive path at a second portion of the conductive path. The electrical connector is configured to functionally couple with an electrical device. A trace is defined by a layer of an insulator material coated over the layer of the second conductor material along a third portion of the conductive path extending between the electrode and the connection. The layer of insulator material encapsulates the third portion of the conductive path between the electrode and the connection.

According to another aspect of the invention, a method of fabricating an electronic textile is provided. Nanoparticles including a first conductor material are deposited on a fabric material using a direct spray custom writing process such that the nanoparticles penetrate the fabric material along a conductive path. A layer of a second conductor material is formed on the deposited nanoparticles to form the conductive path on the fabric material. A layer of a third conductor material is formed on a first portion of the conductive path to define an electrode that is configured to contact and provide an electrical connection with a subject while the subject is wearing the fabric material. A connector is secured to the fabric material at a second portion of the conductive path. The connector is configured to functionally couple with an electrical device. A layer of an insulator material is formed on a third portion of the conductive path. The layer of insulator material encapsulates the third portion of the conductive path and defines a trace between the electrode and the connection.

Technical effects of the electronic textile and method described above preferably include the ability to fabricate custom, high-quality e-textiles with processes that are capable of large-scale production. Other aspects and advantages of this invention will be appreciated from the following detailed description in view of the drawings.

BRIEF DESCRIPTION OF THE DRAWINGS

FIGS. 1B, 1C, and 1D contain SEM images showing aspects of e-textiles produced with the DRSS of FIG. 1A.

FIG. 1E schematically represents an electrically-conductive trace produced with the DRSS of FIG. 1A.

FIG. 5A illustrates an e-textile fabricated using a DRSS of the type represented in FIG. 1A and with steps as outlined in FIGS. 2 and 3 to have electrically-conductive traces connected to electrodes across a large area of a fabric at meter-scale. FIG. 5B illustrates a horse in a custom e-textile of the type shown in FIG. 5A. FIG. 5C schematically represents suitable locations for ECG, EMG, and abdominal strain measurements in a horse with a custom e-textile of the type shown in FIG. 5A. FIG. 5D schematically represents a system for ambulatory health monitoring of multiple horses.

DETAILED DESCRIPTION OF THE INVENTION

Figure 1A:
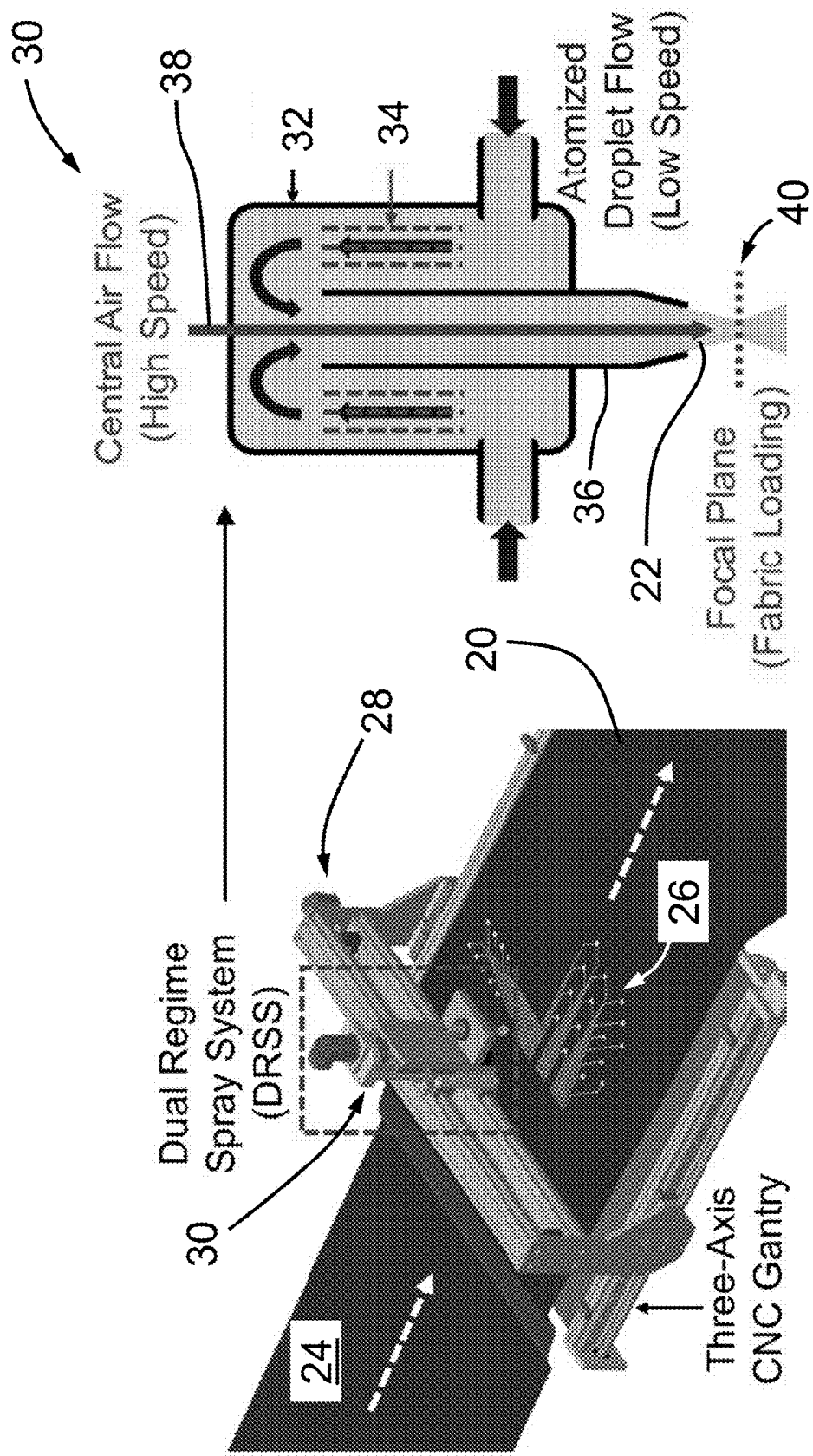
FIG. 1A schematically represents aspects of a nonlimiting method for fabrication of e-textiles, in particular, a dual regime spray (DRS) process performed with a dual regime spray system (DRSS).

The intended purpose of the following detailed description of the invention and the phraseology and terminology employed therein is to describe what is shown in the drawings, which relate to one or more nonlimiting embodiments of the invention, and to describe certain but not all aspects of what is depicted in the drawings, including the embodiment(s) to which the drawings relate. The following detailed description also describes certain investigations relating to the embodiment(s) depicted in the drawings, and identifies certain but not all alternatives of the embodiment(s) depicted in the drawings. As nonlimiting examples, the invention encompasses additional or alternative embodiments in which one or more features or aspects shown and/or described as part of a particular embodiment could be eliminated, and also encompasses additional or alternative embodiments that combine two or more features or aspects shown and/or described as part of different embodiments. Therefore, the appended claims, and not the detailed description, are intended to particularly point out subject matter regarded to be aspects of the invention, including certain but not necessarily all of the aspects and alternatives described in the detailed description.

Although the invention will be described hereinafter in some examples in reference to the horse coverings shown in the drawings, it will be appreciated that the teachings of the invention are also more generally applicable to a variety of types of applications, such as, but not limited to e-textiles to be worn by humans and/or other animals, different electrical circuits, different electronic couplings, and use with different electronic devices.

Disclosed herein is a method for producing large-scale multifunctional e-textiles in a rapid automated manner using a direct spray custom writing process that is capable of depositing functional nanomaterials (nanoparticles) into fabrics, for example, commercial stretch fabrics and garments, to achieve rapid batch production of large-scale and custom-designed e-textiles with various geometric complexities. In certain embodiments, the process employs a dual regime spray (DRS) process performed with a dual regime spray system (DRSS) that includes two separate (e.g., high- and low-speed) air flow modules on a three-axis computer numerical control (CNC) gantry. This arrangement enables the pre-programed direct spraying of conducting nanoparticles into a variety of custom designed pathways of different selected widths, lengths, and/or shapes, on commercial stretch fabrics and garments across a large area (e.g., greater than meter scale) with high mass loading (e.g., up to 18 mg·cm$^{-2}$) and deep penetration (e.g., up to 600 μm-deep). Subsequent application of a waterproof elastomer along the as-sprayed conducting nanoparticles forms a uniform sealing overcoat to provide mechanical and chemical protection against multiple uses and laundry cycles. As such, the method eliminates the need of shadow masks or dedicated vacuum equipment that are often required in existing methods for producing e-textiles.

Figure 2:
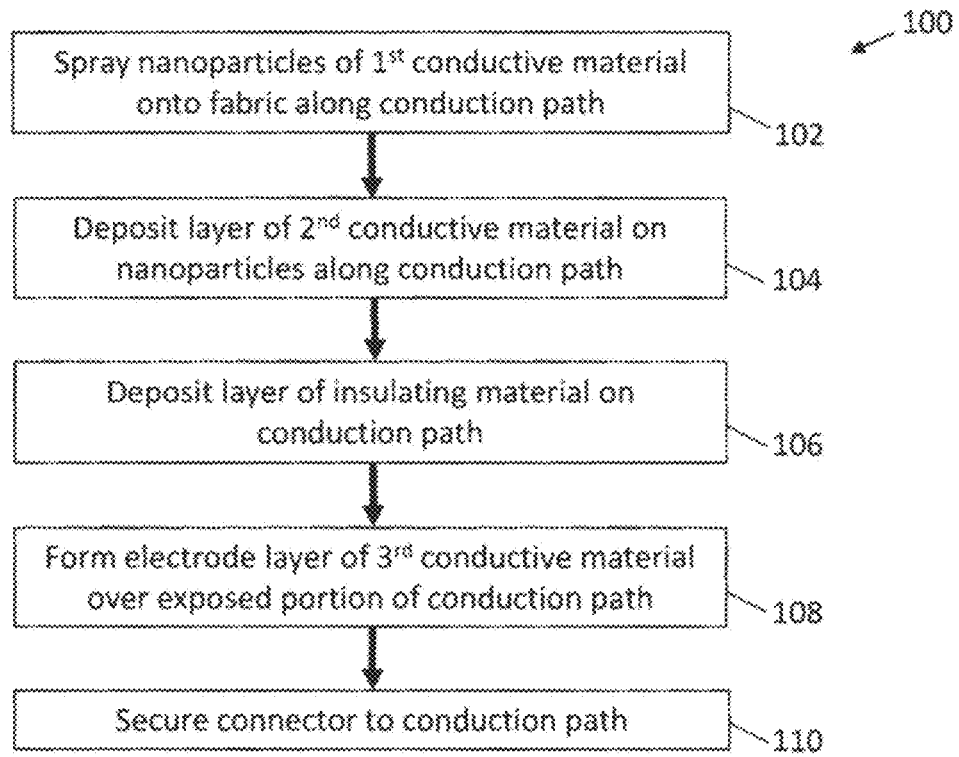
FIG. 2 shows steps an example method for fabrication of an electronic textile in accordance with aspects of the invention.
Figure 3:
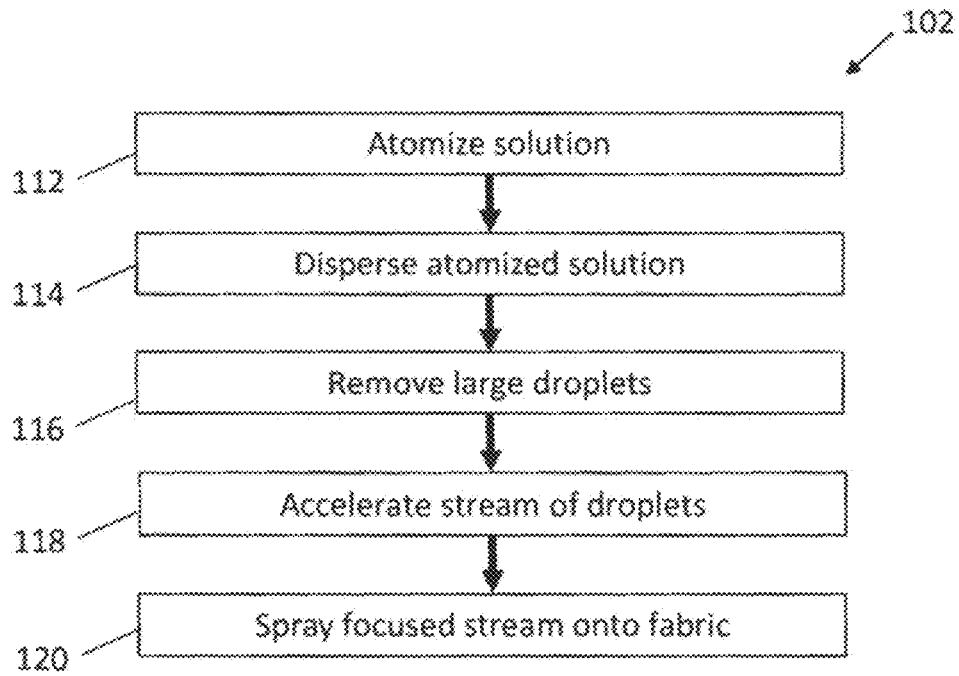
FIG. 3 shows steps in an example dual regime spray process that can be implemented in a direct spray custom writing process of FIG. 2.

Turning now to the drawings, FIG. 1A schematically represents equipment adapted for implementing nonlimiting embodiments of a method 100 for fabricating an e-textile 20 on a fabric (garment) 24, and FIGS. 2 and 3 illustrate nonlimiting example steps in the method 100. In this example, a DRSS 30 is used to deposit components of conductive paths 26 on the fabric 24. An example of such a conductive path 26 is schematically represented in FIG. 1E. In this nonlimiting example, the conductive path 26 comprises an electrically-conductive trace 52, a recording electrode 48 operatively coupled to one end of the trace 52, and an electrical connector 50 operatively coupled to an opposite end of the trace 52 to transmit data or other electrical signals to and/or from the electrode 48.

In FIG. 1A, the DRSS 30 is mounted to a three-axis CNC gantry 28 to deposit nanoparticles 22 of a conductive material onto the fabric 24 along conductive paths 26 of the e-textile 20 being produced. The DRSS 30 atomizes a solution containing the nanoparticles 22 into fine droplets with a pneumatic atomizer, which is schematically represented in FIG. 1A as including a mixing chamber 32 fed by a low-speed air flow to promote uniform dispersion (e.g., reduce cyclone effects) of the nanoparticles 22 within a stream of droplets expelled from a nozzle 36. Before exiting the nozzle 36, the droplets pass through an internal flow-conditioning unit (FCU) 34 to filter and remove large droplets. The remaining droplets exiting the FCU 34 are accelerated through the nozzle 36 by a high-speed central air flow 38 to remain focused at a focal plane 40, enabling narrow and deep penetration of the nanoparticles 22 of the conductive material onto the surface of the fabric 24 and penetrating into the fabric 24 without aggregation.

Referring now to FIG. 2, at 102 the nanoparticles 22 of the conductive material are sprayed onto the fabric 24 where a conductive path 26 is desired using the DDRS 30 represented in FIG. 1A. Referring to FIG. 3, steps are illustrated in an example DRS process for implementing the spraying step of 102. In FIG. 3, the spray process 102 includes at 112 atomizing the solution containing the nanoparticles 22 into fine droplets with the pneumatic atomizer of FIG. 1A. At 114, the atomized droplets are carried in the mixing chamber 32 by the low-speed air flow. At 116, the droplets pass through the FCU 34 to filter and remove large droplets. At 118, the remaining droplets exiting the FCU 34 are accelerated by the high-speed central air flow 38 through the nozzle 36 to remain focused at the focal plane 40, enabling at 120 narrow and deep penetration of the nanoparticles 22 of the conductive material into the fabric 24 without aggregation.

Referring again to FIG. 2, after the nanoparticles 22 have been sprayed onto the fabric 24 where conductive paths 26 are desired, at 104 a layer of an additional conductor material may be deposited (e.g., electroless plating) on the nanoparticles 22 to complete the conductive paths 26. FIG. 1B is an SEM image showing strands of a fabric 24 whose surfaces have been penetrated by nanoparticles 22 of a conductive material as a result of the spraying step 102, over which a layer 42 of an additional conductor material has been deposited as a result of the spraying step 104. Next at 106, an insulator material may be deposited onto the fabric 24 so as to coat the conductive paths 26 to provide electrical insulation, mechanical protection, and a waterproof or water-resistant barrier against multiple uses and laundry cycles of the resulting e-textile 20. FIG. 1C is an SEM image showing a layer 44 of insulator material overlying the nanoparticle-penetrated strands of the fabric 24 of FIG. 1B. The conductor material layer 42 overcoated by the insulator material layer 44 along a conductive path 26 forms an electrically conductive trace 52 (FIG. 1E). Preferably no insulator material is deposited at areas along the conductive paths 26 designated for recording electrodes 48 (FIG. 1E) of the eventual e-textile 20. At 108, a biocompatible and oxidation-resistant conductor material may be deposited (e.g., electroplated) over the exposed surfaces of the conductive paths 26 to form the recording electrodes 50 (FIG. 1E). In FIG. 1D, a layer 46 of gold is shown as the biocompatible and oxidation-resistant conductor material overlying the nanoparticle-penetrated strands of the fabric 24 of FIG. 1B. At 110, a suitable electrical connector 50 is operatively coupled to a portion of each trace 52, for example, to transmit data or other electrical signals to and/or from the recording electrode 48, such that the trace 52 extends from the electrode 48 to the electrical connector 50 as schematically depicted in FIG. 1E.

This embodiment of the method may be used to produce e-textiles 20 based on various types of natural and synthetic fabrics, including cotton, polyester, and Lycra. Other types of fabrics may be used. While the spraying step 102 in this example is implemented with a DRS process, it is envisioned that other types of direct spray writing methods could be used for applying the nanoparticles along only the desired routes of conductive paths 26 over the surface of the fabric 24 without requiring masking. Producing e-textiles 20 with the method 100 may provide some, and preferably all, of the following benefits: (1) long-term durability through the uniform and strong embedment of functional nanomaterials along yarns in fabrics without aggregation or delamination against multiple uses and laundry cycles; (2) reliable electrical connections through the deep penetration of functional nanomaterials into fabrics; (3) high spatial resolution through the fine patterning of functional nanomaterials into desired shapes and sizes; and (4) large-scale batch production through the mask-free writing of custom sensor designs.

Nonlimiting embodiments of the invention will now be described in reference to experimental investigations leading up to the invention. In particular, quantitative and qualitative evaluations were performed to analyze the process-structure-property relationships of various prototype e-textiles 20 and to demonstrate the utility of such e-textiles 20 through remote telehealth monitoring of model large animals, in this instance horses.

For the investigations, a DRS process as outlined in FIGS. 2 and 3 was performed by atomizing a 73 mM of silver nitrate ($AgNO_3$) solution in a 1:15 mixture of water and ethanol by volume into fine droplets (as a nonlimiting example, about 2.7 μm in mass median average diameter) with a pneumatic atomizer (WestMed-0210, WixOne) at a pressure of 70 kPa. In performing step 102 of FIGS. 2 and 3, the atomized droplets were transported through the DRSS 30 of FIG. 1A using a low-speed air flow in the mixing chamber 32 of less than 10 m·sec$^{-1}$ and a high-speed at the exit of the nozzle 36 of greater than 100 m·sec$^{-1}$ to penetrate $AgNO_3$ nanoparticles 22 into fabrics 24.

Figure 6A:
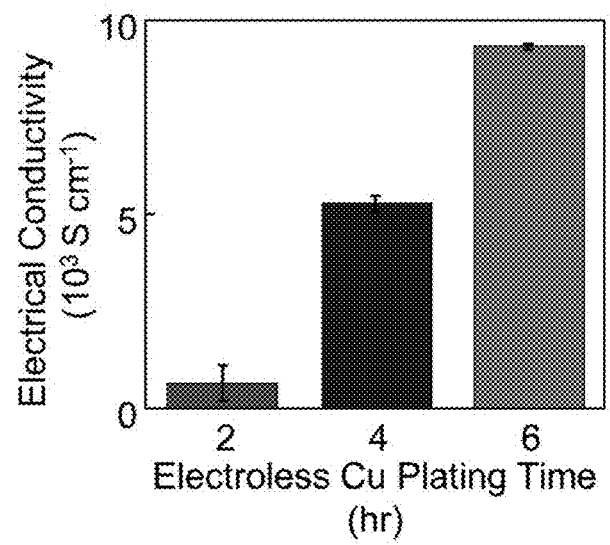
FIG. 6A represents electrical conductivity of a Cu overcoat in a Lycra fabric as a function of electroless Cu plating time, and FIG. 6B contains SEM images of the Cu overcoat in the Lycra fabric.
Figure 6B:
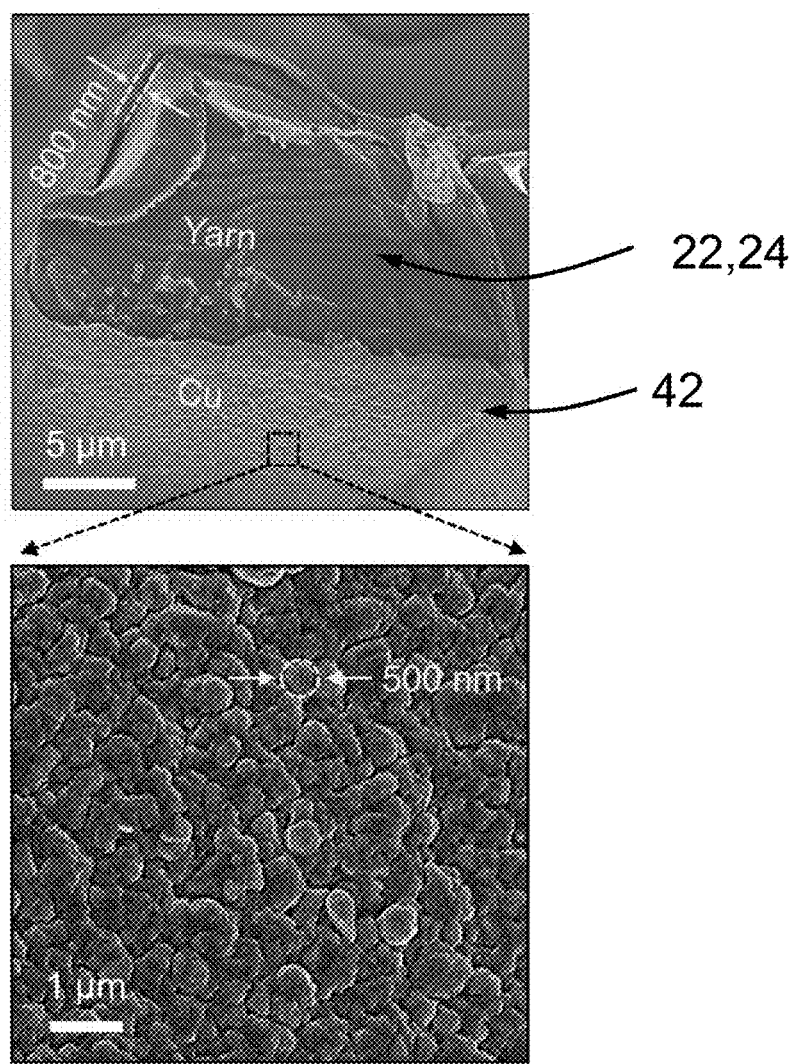

For step 104 of FIG. 2, a conductor material layer 42 of an 800 nm-thick layer of elemental copper (Cu) was electrolessly plated over the sprayed $AgNO_3$ nanoparticles 22 to complete the conductive paths 26. The electroless plating process included immersion of the sprayed fabrics 24 in an electroless copper plating bath at room temperature for six hours. The plating bath was composed of 18 g·L$^{-1}$ of copper (II) sulfate pentahydrate ($CuSO_4 \cdot 5H_2O$; greater than or equal to 98%; Sigma-Aldrich), 48 g·L$^{-1}$ of ethylenediaminetetraacetic acid (EDTA; greater than or equal to 98%; Sigma-Aldrich), 45 g·L$^{-1}$ sodium hydroxide (NaOH; greater than or equal to 97%; Fisher Chemical), 18 mL·L$^{-1}$ of hydrochloric acid (HCl; 1 N; Fisher Chemical), 200 mg·L$^{-1}$ of potassium hexacyanoferrate (II) trihydrate ($K_4Fe(CN)_6 \cdot 3H_2O$; greater than or equal to 99.9%; Sigma-Aldrich), and 20 mL·L$^{-1}$ of formaldehyde (HCHO; 37% aqueous solution; Fisher Chemical). The fabrics 24 were rinsed in water for twenty minutes and dried at room temperature. The electrical conductance of the copper layer increased up to 9,400 S·cm$^{-1}$ after six hours of the electroless plating, resulting in the grain size of 500±37 nm on average. See FIGS. 6A and 6B. Other types of conductive materials and other types of deposition processes could be used.

For step 106 of FIG. 2, the Cu-plated conductive paths 26 in the fabrics 24 were covered with a 60 μm-thick insulator material layer 44 of a silicone rubber commercially available under the Trademark Ecoflex™ 00-30 produced by Smooth-On, Inc., and cut to size using a three-axis CNC router in a pre-programmed manner. The Ecoflex insulator material layer 44 was cured at room temperature. Other types of insulative coatings could be used, and other types of deposition methods could be used.

For step 108 of FIG. 2, the areas of the recording electrodes 48 (which were not covered by the insulator material layer 44) were then coated with a layer 46 of gold (Au) in a brush-type electroplating solution (24 K brush gold gel solution, Gold Plating Services) at 5 V for one minute to form a 1.5 μm-thick layer electrode 48. The resulting e-textiles 20 were rinsed in water for twenty minutes and dried in air. Other types of conductive materials could be used for forming the electrodes 48, and other types of deposition methods could be used.

For step 110 of FIG. 2, standard snap button ends were secured at the ends of traces 52 using a waterproof textile adhesive (Liquid Stitch) to form the electrical connectors 50. Other types of electrical connectors 50 could be used.

Referring again to FIGS. 1B, 1C, and 1D, which are scanning electron microscopy (SEM) images at cross-sections of conductive paths 26 formed by the DRSS 30 of FIG. 1A and processes of FIGS. 2 and 3. FIG. 1B shows the sprayed $AgNO_3$ nanoparticles 22 in a Lycra fabric 24 after the subsequent overcoating of copper (Cu) as the conductor material layer 42 and forming a conductive path 26 before coating with the insulator material layer 44. FIG. 1C shows the Ecoflex insulator material layer 44 encapsulating the conductive path 26 and forming a trace 52. FIG. 1D shows gold (Au) as the layer 46 of biocompatible and oxidation-resistant conductor material coated onto a portion of the conductive path 26 that is not encased in the Ecoflex insulator material layer 44 to form a portion of an electrode 48. The overcoating quality at each step was confirmed by X-ray diffraction (XRD) and energy-dispersive X-ray spectroscopy (EDX) inspections. The process was performed on various types of natural and synthetic fabrics 24, including cotton, polyester, and Lycra, without noticeable difference in overcoating quality.

Figure 4A:
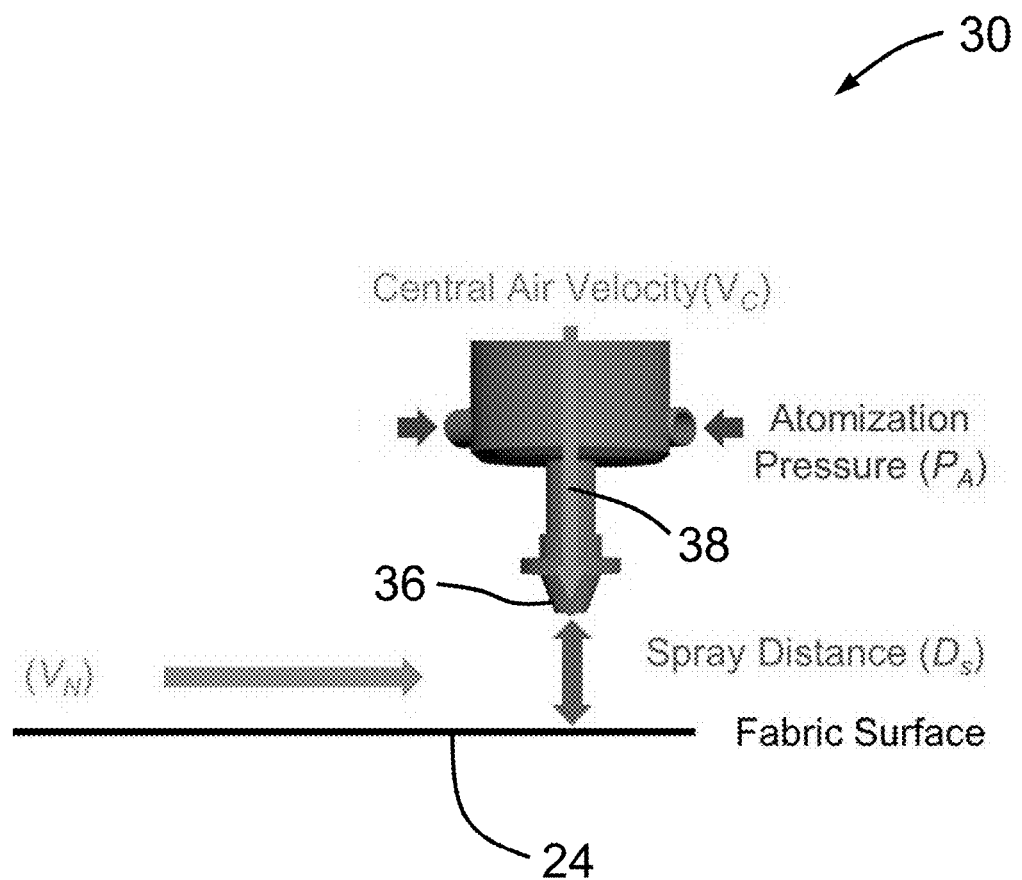
FIGS. 4A through 4C represent (FIG. 4A) governing operational parameters in the process of FIG. 1A and results of experimental investigations analyzing such parameters, including (FIG. 4B) effects of the governing operational parameters on spray resolution, and (FIG. 4C) mass load, penetration depth, and electrical resistance of test units as a function of atomization pressures and spray distances.
Figure 4B:
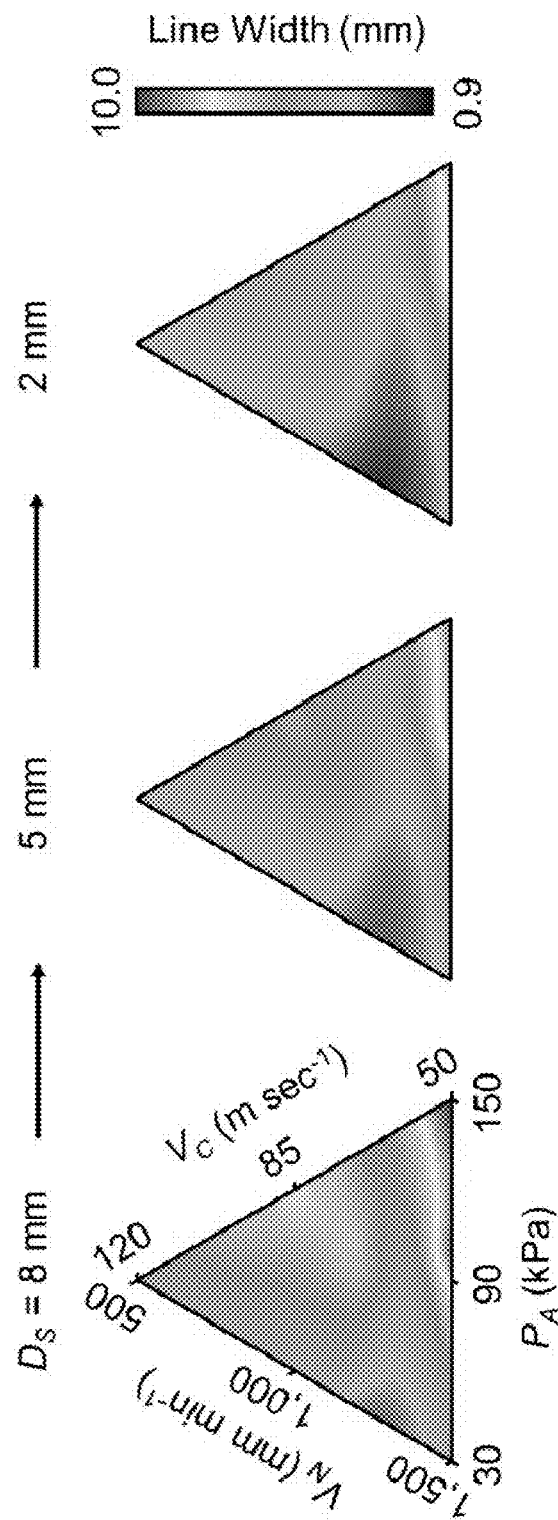
Figure 7A:
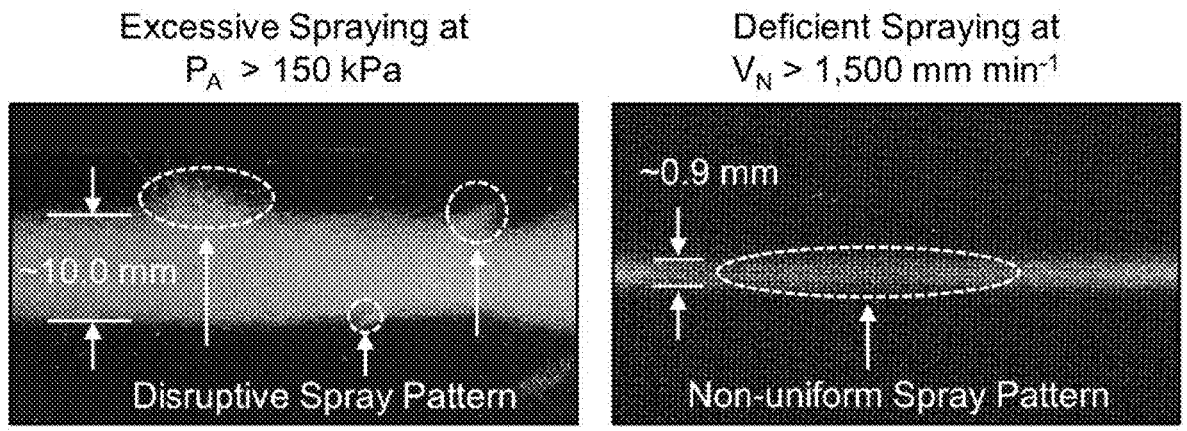
FIGS. 7A and 7B represent images of excessively (left panel) and deficiently (right panel) sprayed electrically-conductive traces (FIG. 7A), and an image of an optimally sprayed electrically-conductive trace (FIG. 7B).
Figure 7B:
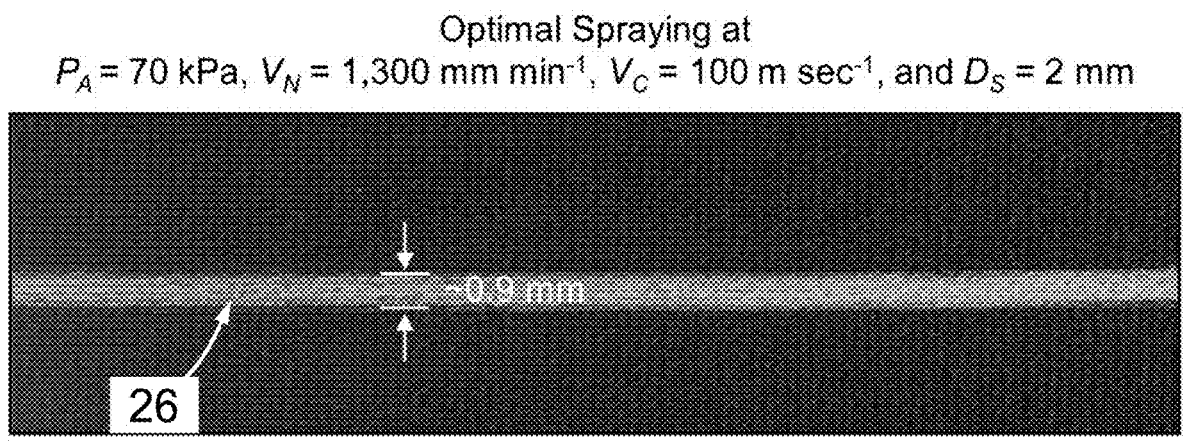

The line width (e.g., 0.9-10 mm) of the nanoparticles 22 along the conductive path(s) 26, penetration depth (e.g., greater than 600 μm-deep) of the nanoparticles 22 below the surface of the strands of the fabric 24, and shape (e.g., straight and/or curvilinear lines) of the conductive paths 26 in the fabrics 24 may be controlled via adjustment of the operational parameters of the DRSS 30 during the DSR process. FIG. 4A schematically represents certain governing operational parameters of the DSR process including atomization gauge pressure ($P_A$), nozzle transverse speed ($V_N$), central air velocity ($V_C$), and spray distance to fabrics ($D_S$). FIG. 4B represents measured effects of the governing operational parameters on spray resolution (e.g., line width) in a range of $P_A$=30 to 150 kPa, $V_N$=500 to 1,500 mm·min$^{-1}$, $V_C$=50 to 120 m·sec$^{-1}$, and $D_S$=2 to 8 mm. The spray resolution was observed to increase with decreased $P_A$ or increased $V_C$ due to the narrow and deep interaction of the sprayed droplets with the fabrics. Deep penetration throughout the fabrics 24 with the thickness of up to 600 μm occurred at $P_A$=70 kPa and $V_C$=100 m·sec$^{-1}$. The highest $V_N$ without disrupting the spray resolution was 1,300 mm·min$^{-1}$ within a single working area (e.g., frame size of the CNC gantry) of 75×120 cm$^2$ at a time. Excessive rise in $P_A$ or $V_N$ beyond a threshold (e.g., greater than 150 kPa or greater than 1,500 mm·min$^{-1}$) resulted in disruptive or non-uniform spray patterns due to the excessively or deficiently sprayed droplets, respectively, as shown in FIG. 7A. The spray resolution increased up to 0.9 mm (e.g., the minimum line width) with increased $V_C$ up to 100 m·sec$^{-1}$ at fixed $P_A$=70 kPa and $V_N$=1,300 mm·min$^{-1}$, as shown in FIG. 7B. Under this condition, the focal plane 40 was formed at $D_S$=2 mm.

Figure 8:
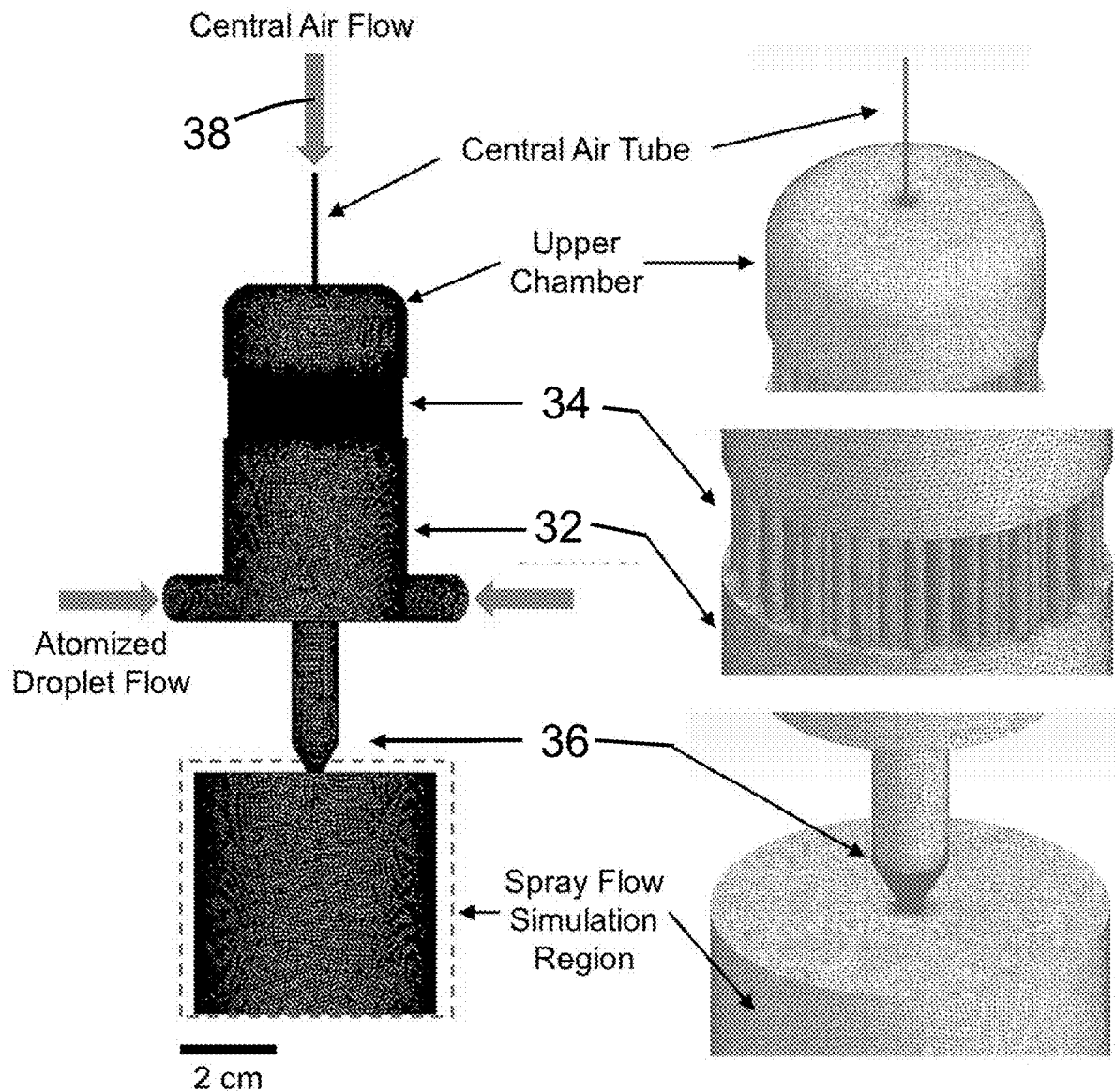
FIG. 8 schematically represents computational domain and local grid of computational fluid dynamics (CFD) modeling.

Experimental and computational fluid dynamics (CFD) results confirmed that the spray flow was focused at the focal plane 40 (e.g., $D_S$=2 mm). The computational domain and local grid of the CFD modeling are shown in FIG. 8. Taken together, the highest spray resolution occurred at the optimal condition of $P_A$=70 kPa, $V_N$=1,300 mm·min$^{-1}$, $V_C$=100 m·sec$^{-1}$, and $D_S$=2 mm. In this condition, the focal plane 40 was coincident with the fabric at the location on the fabric where the nanoparticles are being sprayed.

Figure 4C:
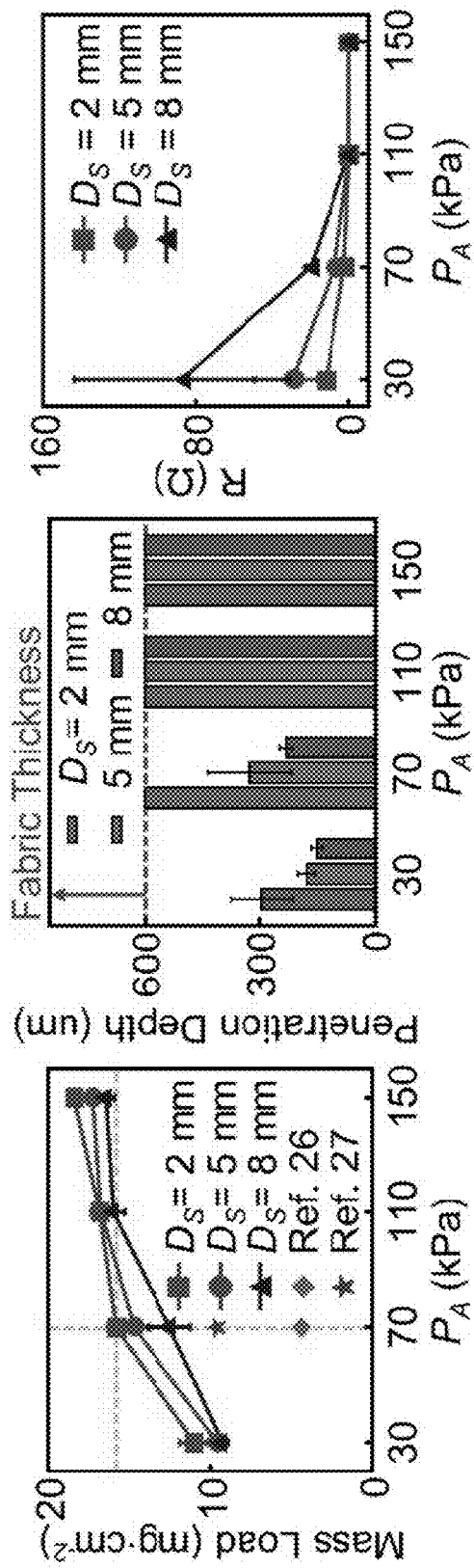

FIG. 4C presents the effect of $P_A$ and $D_S$ on mass load of the nanoparticles 22 (left panel), penetration depth of the nanoparticles 22 into the fabric 24 (middle panel), and electrical resistance of the nanoparticles (right panel) using test units (e.g., a conductive path in a size of 1.3 mm×50 mm) that were sprayed in a Lycra fabric 24. The mass load increased as $P_A$ increased to reach the maximum (about 18 mg·cm$^{-2}$) at $D_S$=2 mm, which is substantially higher than those reported in previous studies. The penetration depth also increased as $P_A$ increased where the deep penetration (greater than 600 μm) into fabrics occurred with $P_A$ greater than or equal to 70 kPa at $D_S$=2 mm and occurred with $P_A$ greater than or equal to 110 kPa at $D_S$=5 mm and at $D_S$=8 mm. The high mass load and deep penetration resulted in sufficiently low electrical resistance (less than 2.6 Ω·cm$^{-1}$) at the optimal condition, and were likely attributed to the kinetic energy gain of the atomized droplets (about 2.7 μm in mass median average diameter) at high atomization pressure ($P_A$>70 kPa).

The implementation of e-textiles in ambulatory health monitoring applications typically requires their continuous intimate contact to the skin against periodic strain cycles (e.g., on-body movements). In addition, their long-term use in clinical practice also typically requires a sufficient level of wearability, durability, and comfort. Certain commercially available stretch fabrics and/or garments meet these requirements as they are breathable (i.e., air permeable), durable, and intrinsically stretchable to conform to a variety of body sizes and shapes with seamless fits. Therefore, there is a particular interest in converting commercially available stretch fabrics and garments into multifunctional e-textiles 20.

To accomplish this goal, the DRS process of FIG. 1A was applied to a highly elastic Lycra fabric (Schneiders) to generate test units, for example, having a conductive path 26 in a size of 1.3 mm×50 mm. Various benchtop tests were performed on sample e-textiles 20 fabricated with the method of FIG. 1, including $R/R_0$ of test units under stretching up to 50%, $R/R_0$ of test units under folding and unfolding, $R/R_0$ of test units under twisting and untwisting up to 360 degrees, and $R/R_0$ of test units under a total of ten laundry cycles with and without the presence of the Ecoflex insulator material layer 44. The mechanical modulus of test units with and without the presence of the insulator material layer 44 as compared to a bare Lycra fabric 24 was tested. The mechanical moduli of the test units were nearly identical as compared to the bare Lycra fabric (E about 1.5 kPa), which increased up to 6.1 kPa with the presence of the Ecoflex insulator material layer 44. The relative resistance change ($R/R_0$) of the test units (n=3 for each group) was measured when stretched up to the intrinsic stretch limit (about 50%) of the Lycra fabric along three different directions: (1) wale (i.e., to the lengthwise column of the meandering loops), (2) diagonal, and (3) course (i.e., to the crosswise row of the meandering loops). No substantial change in $R/R_0$ appeared regardless of stretching direction. Irreversible fabric damage occurred when stretched beyond 50% mostly along diagonal and course directions, leading to the exponential increase of the $R/R_0$. Notably, the $R/R_0$ only slightly changed when stretched even up to 150% along wale direction, which may be attributed to the ultra-low effective modulus (about 2.3 kPa) of the constituent "horseshoe"-like filamentary columns in the Lycra fabric that underwent large-scale, bending-dominant deformation when stretched along wale direction. The maximum principal strains obtained from the finite element modeling (FEM) were 0%, 15.6%, and 38.5% at the elongation of 0%, 25%, and 50%, respectively. Consistently, the $R/R_0$ only slightly changed against folding and twisting up to 360°. In all cases, no noticeable differences appeared in deformation behaviors as compared to the bare Lycra fabric, exhibiting negligible or insignificant changes in the $R/R_0$ after 1,000 cycles. The impact of multiple laundry cycles on the $R/R_0$ with and without the presence of the Ecoflex insulator material layer 44 was tested using a commercially-available washing machine. Each laundry cycle involved the following steps: (1) 10-minute spinning in warm water at 30° C. with a fabric detergent (1 mg·mL$^{-1}$; Jacquard Synthrapol); (2) 5-minute rinsing in cold water, and (3) 2-minute spin-drying at room temperature. At least 3-hour sun-drying was followed for complete dry. The $R/R_0$ only slightly changed throughout a total of ten laundry cycles with the presence of the Ecoflex insulator material layer 44. The results imply that no material loss occurred during or after the laundry cycles. On the other hand, a substantial increase in the $R/R_0$ occurred after each laundry cycle without the presence of the Ecoflex insulator material layer 44 due to irreversible fabric damages (e.g., rips) or oxidations (e.g., color change).

Increasing demand for the at-home care of farm or household animals calls for an effective wearable sensing platform to continuously collect vital health signals under ambulatory conditions. Despite the great promises of e-textiles in this context, a rapid batch production of custom sensor designs remains limited particularly at large scale. To address this issue, a pilot study entailing in vivo evaluations was carried out with a wearable sensing platform 54 including the DSR production of custom multimodal sensors incorporated into commercially-available stretch horse blankets with tailored sensor designs for the continuous monitoring of heart activity, muscle movement, and respiration pattern in a horse model.

Figure 5A:
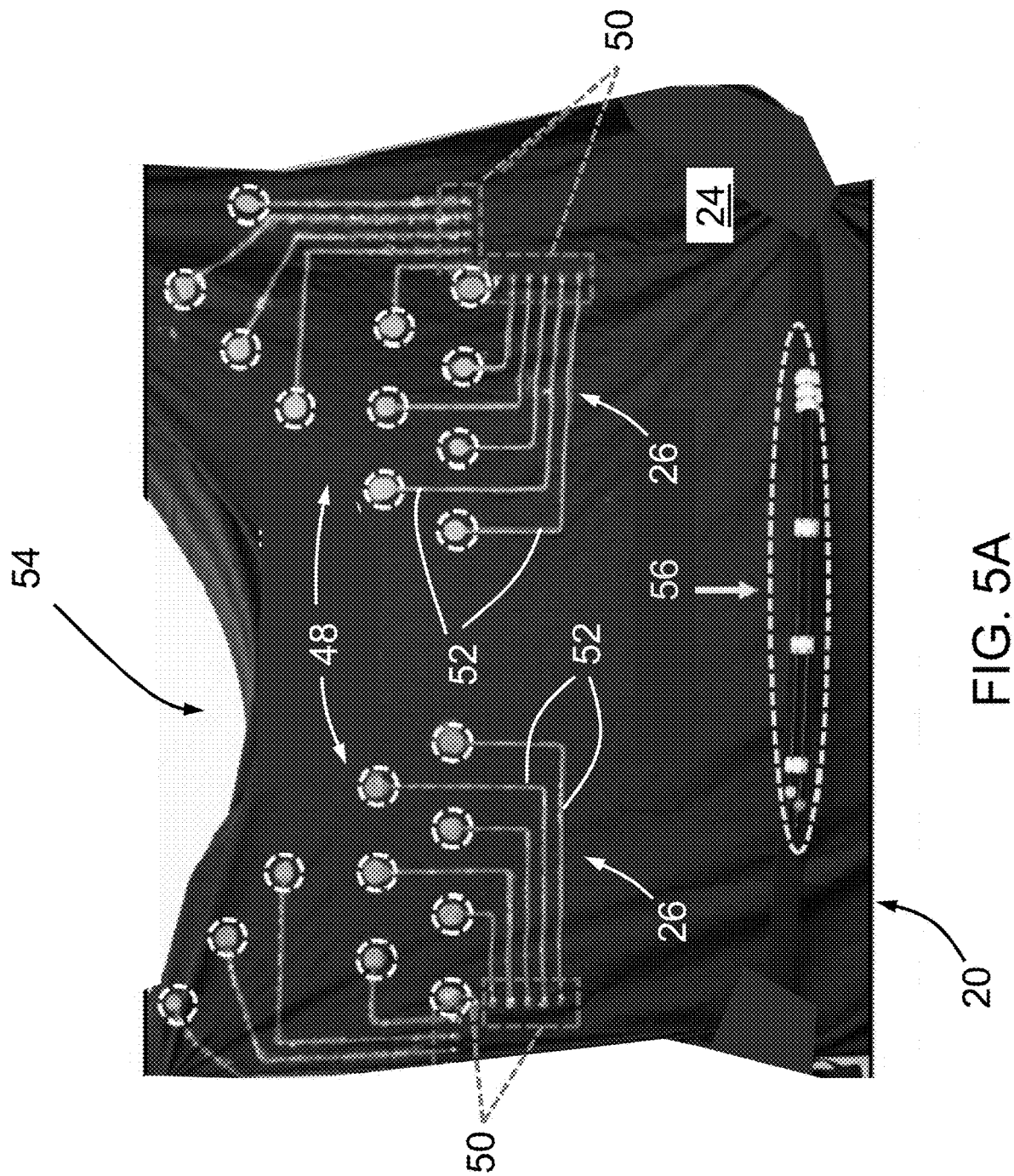
FIGS. 5A through 5D represent aspects of a pilot study of e-textiles fabricated with a method of the present invention in a large animal model.
Figure 5B:
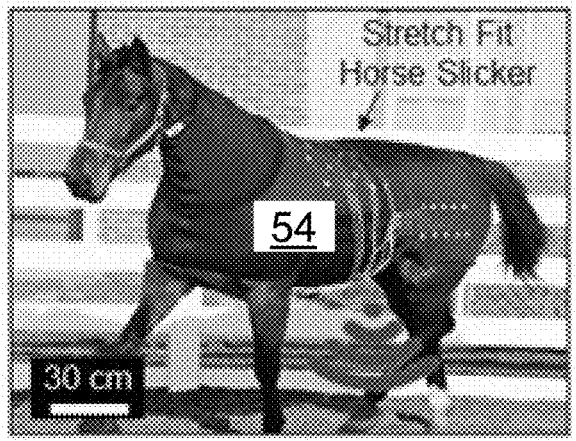
Figure 5C:
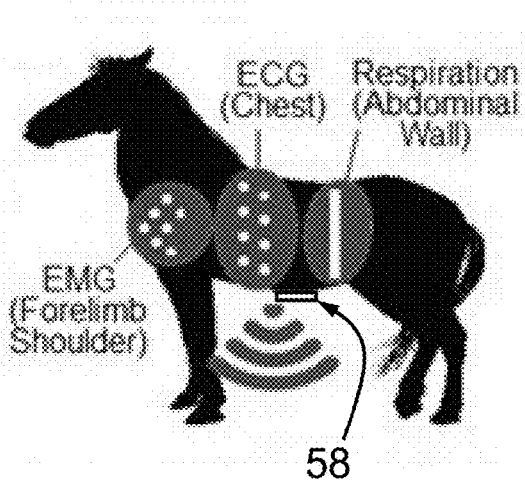

FIG. 5A illustrates an e-textile 20 fabricated using a DRSS of the type represented in FIG. 1A and with steps as outlined in FIGS. 2 and 3 to have conductive paths 26 comprising electrically-conductive traces 52 connected to recording electrodes 48 and electrical connectors 50 across a large area of a fabric 24 (a stretch horse blanket), yielding a custom e-textile 20 capable of use as a sensing platform 54 wearable by a large animal, such as a horse. The sensing platform 54 was further fabricated to include strain gauges 56. FIG. 5B is an image of a horse wearing a sensing platform 54 similar to what is shown in FIG. 5A and made from a custom e-textile 20 constructed of a commercially-available stretch horse blanket (Lycra fabric; Schneiders) as the fabric 24. The e-textile 20 was configured into a tailored sensor design to meet specific geometric demands of the wearable sensing platform 54 in order to obtain simultaneous measurement of electrocardiogram (ECG) signals (e.g., heart activity), electromyogram (EMG) signals (e.g., muscle movement), and abdominal strains (e.g., respiration pattern) from the chest, forelimb shoulder, and abdominal wall of the horse, respectively, as illustrated in FIG. 5C. A total of twenty-one recording electrodes 48 and two strain gauges 56 were rationally distributed across the entire area (100 cm×130 cm) of the surface of the fabric 24, similar to what is shown in FIG. 5A. A total of twenty-one snap button ends (Florida Research Instruments) were secured using a waterproof textile adhesive (Liquid Stitch) on the peripheral edge of the fabric 24 in a minimally obtrusive manner to serve as the connectors 50. The snap button ends were used for wire connections to a custom-built portable data acquisition unit 58 (74 cm×58 mm×32 mm; 150 g) clipped to the sensing platform 54. Several of the snap button ends were appropriately chosen to define desired measurement locations by considering horse-by-horse variations in body size and shape. The portable data acquisition unit 58 was modified from a commercial unit (BioRadio, GLNeuroTech Inc.), allowing for (1) multichannel data acquisition (up to 8 single-ended channels) at a sample rate of 250 to 16,000 Hz; (2) battery powering with the capacity of 420 mAh at 3.7 V; and (3) wireless (e.g., Bluetooth®) data communications at 190 kbps within the maximum transmission range of 30 meters.

Several different designs of wearable sensing platforms 54 made from the e-textiles 20 were produced in various types of stretch horse blankets, including full zip blanket hood made of stretchable Lycra (shown at top), faceless pull-on full body blanket made of stretchable Lycra (shown at middle), and mesh full zip blanket hood made of polyester polar fleece (shown at bottom), without noticeable difference in quality. For all the cases, no sign of discomfort or irritation was observed in the horses while freely walking, trotting, and galloping in a round pen or resting and eating in a stall.

Figure 5D:
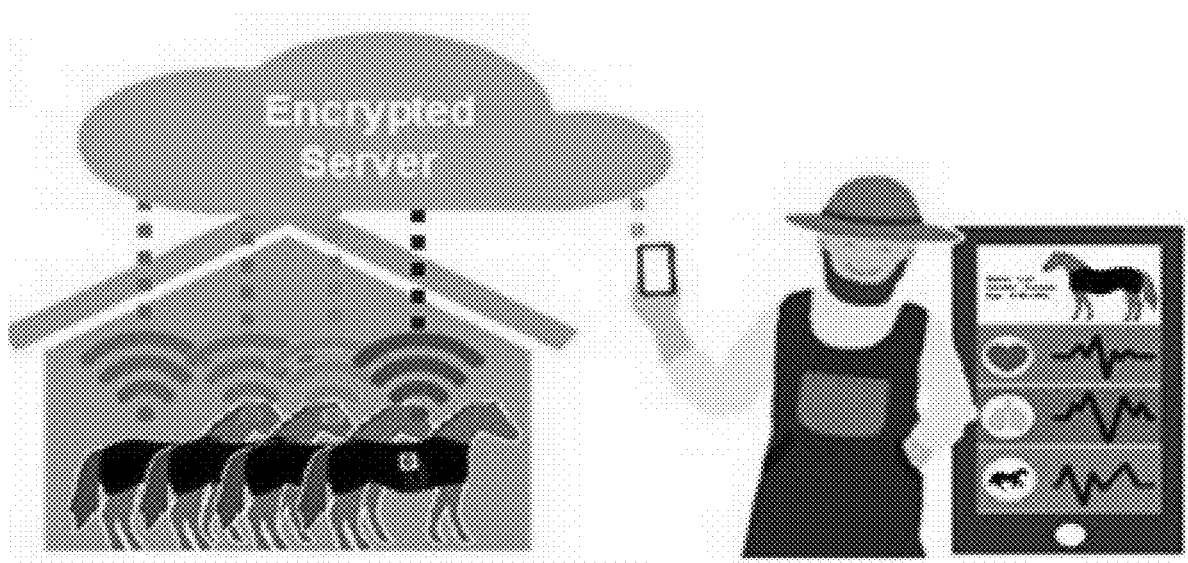

FIG. 5D schematically represents a system for the ambulatory health monitoring of multiple horses, supported by wireless (Bluetooth®) communications with a caregiver via an encrypted server. In the in vivo evaluations, Standardbred female horses (n=2; 11 to 16 years old; 417 to 449 kg) were monitored using the modified horse blankets. The horses were considered healthy with the median body condition score of greater than 5 out of 9 points. Prior to this study, the horses were trained to perform standardized exercises such as walking, trotting, and galloping during lunging in a round pen. The horses were housed in a stall, fed hay, and bedded on shavings.

Various ambulatory data were recording from the pilot study of FIGS. 5A through 5D, including measurements of ECG and EMG signals in a horse while walking, measurements of abdominal strains as compared to control measurements using a conventional pneumotachograph and time-series and spectral dataset of heart rate, respiration rate, and forelimb movement in a horse while eating, wandering, and resting for 90 minutes. The measurement of ECG and EMG signals were obtained from the upper, middle, and lower chest and the left and right forelimb shoulders of a horse under ambulatory conditions. Both the ECG and EMG signals were captured on the skin, without shaving haircoat, at a sampling rate of 1 kHz per channel with 24-bit resolution. A reference (ground) electrode was placed on tarsal bone. For the measurements, an electrolyte gel (Parker) was applied to the recording electrodes 48 for enhanced electrical contact to the skin. The ECG signals exhibited no delay between P and QRS-waves. The recording electrodes in the e-textiles exhibited an electrical impedance of 121 to 442Ω in a bandwidth of 20 to 500 Hz which is within a typical range of commercial recording electrodes (250 to 374Ω). For control measurements, commercial equine self-adhesive electrodes (H124SG; Covidien) were attached to the skin after shaving haircoat to reduce noise level. The wearable sensing platform 54 made with the e-textiles 20 maintained a seamless, tight interface with the skin under ambulatory conditions even without the use of adhesives, enabling the high-fidelity recording of ECG and EMG signals. In turn, the signal quality in terms of the amplitude, duration, and relative onset and offset times of the ECG and EMG signals was comparable between the measurements using the e-textiles 20 and the control recording electrodes without and with shaving haircoat, respectively. Occasional motion artifacts were observed in the ECG signals during abrupt changes in body postures, which was alleviated by applying a sufficient amount (greater than or equal to 2 g) of the electrolyte gel. Measurements of abdominal strains (e.g., respiration pattern) were obtained using the strain gauges 56 in the e-textiles 20 and compared to control measurements using a conventional pneumotachograph (#4 Fleisch; EMKA Technologies).

Figure 9B:
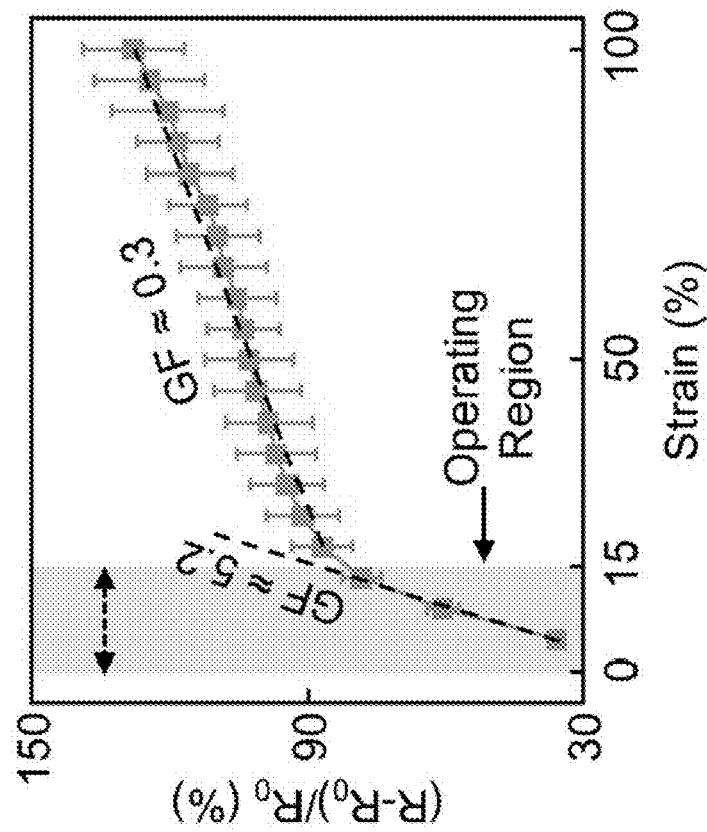
FIG. 9B plots gauge factor measurements at applied strains of up to 100%.
Figure 9A:
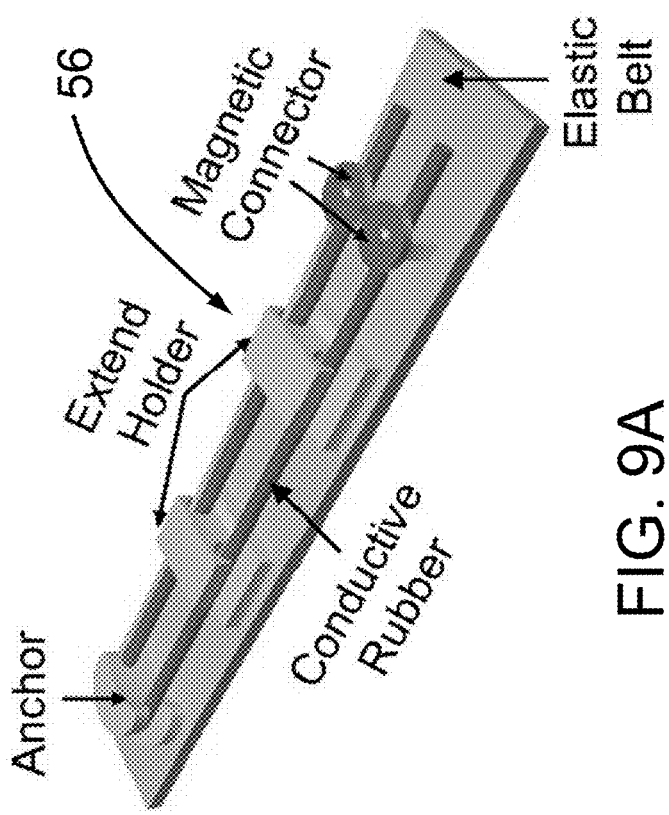
FIG. 9A is a schematic illustration of a strain gauge.
Figures 9C, 9D:
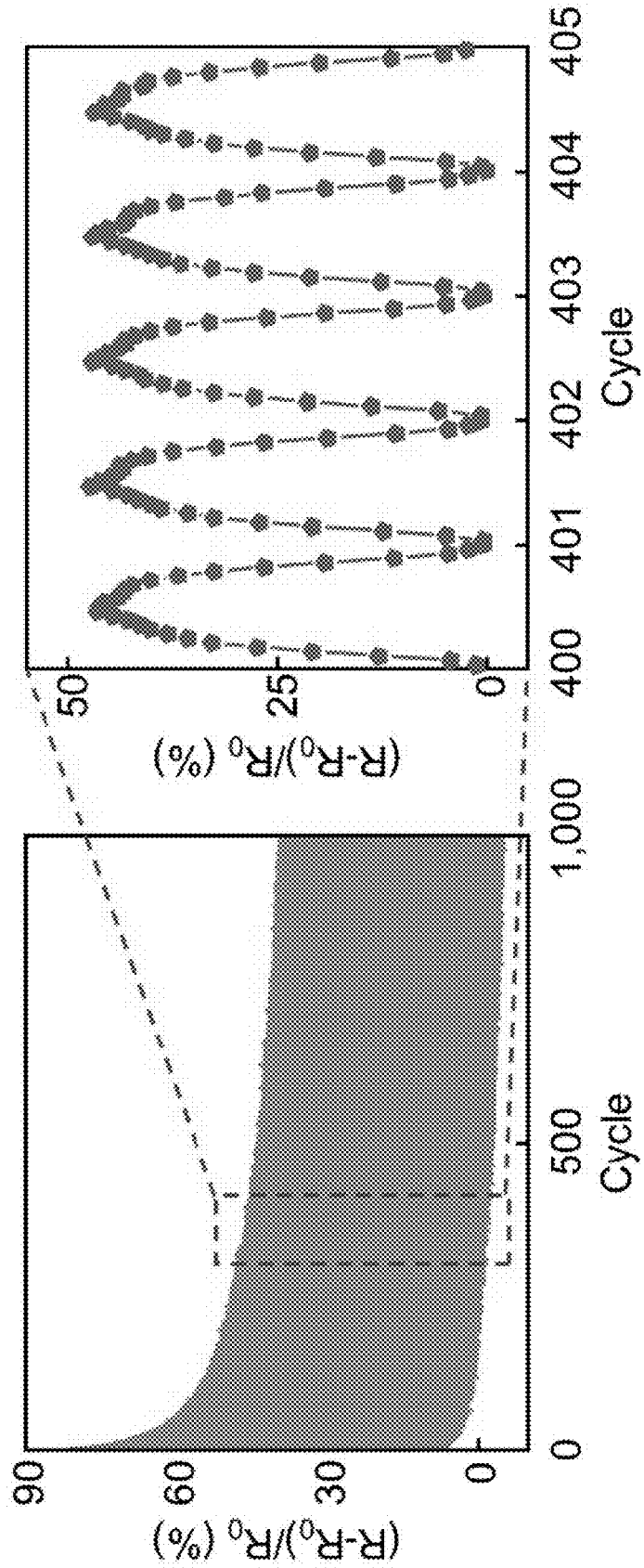
FIGS. 9C and 9D plot $R/R_0$ of the strain gauge.

FIG. 9A shows an example strain gauge 56. The gauge factor of the strain gauges 56 was measured as 5.2 at the applied strain ranging from 0 to 15%, as shown in FIG. 9B. FIGS. 9C and 9D plot $R/R_0$ of the strain gauges 56. The pneumotachograph was inserted in a facemask placed on the muzzle of the horse. The pneumotachograph was wired to an external differential pressure transducer (DP-/45-14; Validyne Engineering) while the horse was tethered still during the measurements. The tethered measurements inevitably posed discomfort and disruption in continuous recording under ambulatory conditions as also observed in previous studies using the pneumotachograph. Both the strain and respiratory airflow waveforms were clearly distinguishable with respect to inspiratory and expiratory abdominal movement, exhibiting a respiration rate of 12 breaths per minute under the condition. The time-series and spectral dataset of heart rate, respiration rate, and forelimb movement in the horse while resting in a stall for 90 minutes were recorded.

The average heart rate and respiration rate were measured as 40 bpm and 24 breaths per minute, respectively. The forelimb movement was also clearly distinguishable without showing substantial motion artifacts through bandpass filtering at the cut-off frequency of 20 to 500 Hz.

A particular utility of the e-textiles 20 and/or wearable sensing platform 54 made from the e-textiles may also exist in the routine ambulatory monitoring of cardiac and muscle activity in horse athletes to better understand exercise physiology in daily practical training. To demonstrate this, the quantitative details of ambulatory ECG and EMG signals obtained from the chest and forelimb shoulders of a horse while trotting, walking, and resting in an arena for fifteen minutes in a random order were recorded using the wearable sensing platform 54. The high-fidelity recording of the signals was maintained throughout the entire testing period without any sign of discomfort or irritation in the horse. All the signals were simultaneously collected through multi-channel data acquisitions at a sampling frequency of 1 kHz per channel from a distance via Bluetooth® communications. The power consumption for the wireless monitoring was approximately 50 mA with a battery life of up to eight hours on a single charge.

The methods and e-textiles disclosed herein represent a platform technology for converting existing fabrics, garments, and materials therefor into large-scale and custom-designed e-textiles 20 without compromising the intrinsic fabric properties in terms of wearability, durability, and comfort. Wearable sensing platforms 54 made from the resulting e-textiles 20 can fit tightly to the skin of bodies of various sizes and shapes, while anchoring the recording electrodes 48 in place under ambulatory conditions. Leveraging these features, the e-textiles 20 provide excellent measurement accuracy and fidelity in capturing physiological and electrophysiological signals beyond conventional measurement methods. Pilot field tests in horses under ambulatory conditions demonstrated the utility of the e-textiles 20 in a remote telehealth monitoring setting. Further, use of the e-textiles 20 of the present invention are not limited to horses, and may be used for applications on humans and other types of animals, for example as part of a wearable sensing platform 54 that is customed designed for different functions on a different subject body. Key outcomes showed the potential for rapid batch production of e-textiles, which will be critically important for wide adoption in clinical practice.

As previously noted above, though the foregoing detailed description describes certain aspects of one or more particular embodiments of the invention and investigations associated with the invention, alternatives could be adopted by one skilled in the art. For example, the e-textiles 20 and their components could differ in appearance and construction from the embodiments described herein and shown in the figures, functions of certain components of the e-textiles 20 could be performed by components of different construction but capable of a similar (though not necessarily equivalent) function, process parameters such as temperatures and durations could be modified, and appropriate materials could be substituted for those noted. As such, and again as was previously noted, it should be understood that the invention is not necessarily limited to any particular embodiment described herein or illustrated in the drawings.

The invention claimed is:

1. An electronic textile, comprising:
    a fabric material configured to be worn by a subject;
    a conductive path that includes nanoparticles comprising
        a first conductor material penetrated into the fabric material along the conductive path and a layer of a second conductor material coated over the nanoparticles along the conductive path;
    an electrode electrically coupled with the conductive path, wherein the electrode comprises a layer of a third conductor material coated over the layer of the second conductor at a first portion of the conductive path, wherein the electrode is configured to contact and provide an electrical connection with the subject while the subject is wearing the fabric material;
    an electrical connector secured to the fabric material and electrically coupled with the conductive path at a second portion of the conductive path, wherein the electrical connector is configured to functionally couple with an electrical device; and
    a trace defined by a layer of an insulator material coated over the layer of the second conductor material along a third portion of the conductive path extending between the electrode and the connection, wherein the layer of insulator material encapsulates the third portion of the conductive path between the electrode and the electrical connector.

2. The electronic textile of claim 1, wherein the nanoparticles penetrate the fabric material to a depth of greater than 600 μm.

3. The electronic textile of claim 1, wherein the first conductor material comprises silver nitrate ($AgNO_3$).

4. The electronic textile of claim 1, wherein the second conductor material comprises copper (Cu).

5. The electronic textile of claim 1, wherein the insulator material comprises silicone rubber.

6. The electronic textile of claim 1, wherein the third conductor material comprises a biocompatible and oxidation-resistant conductor material.

7. The electronic textile of claim 1, wherein the fabric material comprises at least one of cotton, polyester, and Lycra.

8. The electronic textile of claim 1, wherein the nanoparticles have a mass loading on the fabric material of up to 18 mg cm$^{-2}$.

9. The electronic textile of claim 1, wherein the nanoparticles have an electrical resistance of less than 2.6 Ω.

10. The electronic textile of claim 1, wherein the electric device comprises a data acquisition device.

11. The electronic textile of claim 1, wherein the conductive path has a width between about 0.9 mm and about 10 mm.

12. The electronic textile of claim 1, wherein the conductive path comprises curvilinear portions.

13. A method of fabricating an electronic textile, the method comprising:
    depositing nanoparticles comprising a first conductor material on a fabric material using a direct spray custom writing process such that the nanoparticles penetrate the fabric material along a conductive path;
    forming a layer of a second conductor material on the deposited nanoparticles to form the conductive path on the fabric material;
    forming a layer of a third conductor material on a first portion of the conductive path to define an electrode that is configured to contact and provide an electrical connection with a subject while the subject is wearing the fabric material;
    securing a connector to the fabric material at a second portion of the conductive path, wherein the connector is configured to functionally couple with an electrical device; and forming a layer of an insulator material on a third portion of the conductive path, wherein the layer of insulator material encapsulates the third portion of the conductive path and defines a trace between the electrode and the connector.

14. The method of claim 13, wherein the direct spray custom writing process comprises a dual regime spray process comprising:
- atomizing a solution comprising the first conductive material into droplets with a pneumatic atomizer;
- passing the droplets through a mixing chamber of a dual regime spray system having a low-speed air flow to promote uniform dispersion of the droplets;
- passing the droplets through an internal flow-conditioning unit of the dual regime spray system to filter and remove relatively large droplets of the droplets;
- passing a stream of the droplets through a high-speed region of the dual regime spray system; and
- spraying a focused stream of the droplets from an exit nozzle of the dual regime spray system onto the fabric material.

15. The method of claim 14, further comprising moving the dual regime spray system with a three-axis computer numerical control gantry coupled thereto to selectively deposit the nanoparticles on the fabric material along the conductive path.

16. The method of claim 13, wherein depositing the nanoparticles comprises spraying the first conductor material along a curvilinear path onto the fabric material.

17. The method of claim 13, wherein forming the layer of the second conductor material comprises an electroless plating process.

18. The method of claim 13, wherein forming the layer of the third conductor material comprises an electroplating process.

19. The method of claim 13, wherein the step of spraying comprises focusing the stream at a focal plane coincident with the fabric material where the nanoparticles are being deposited.

* * * * *